May 23, 1950 W. E. LAMMERTS Plant Pat. 943
ROSE PLANT
Filed March 15, 1949
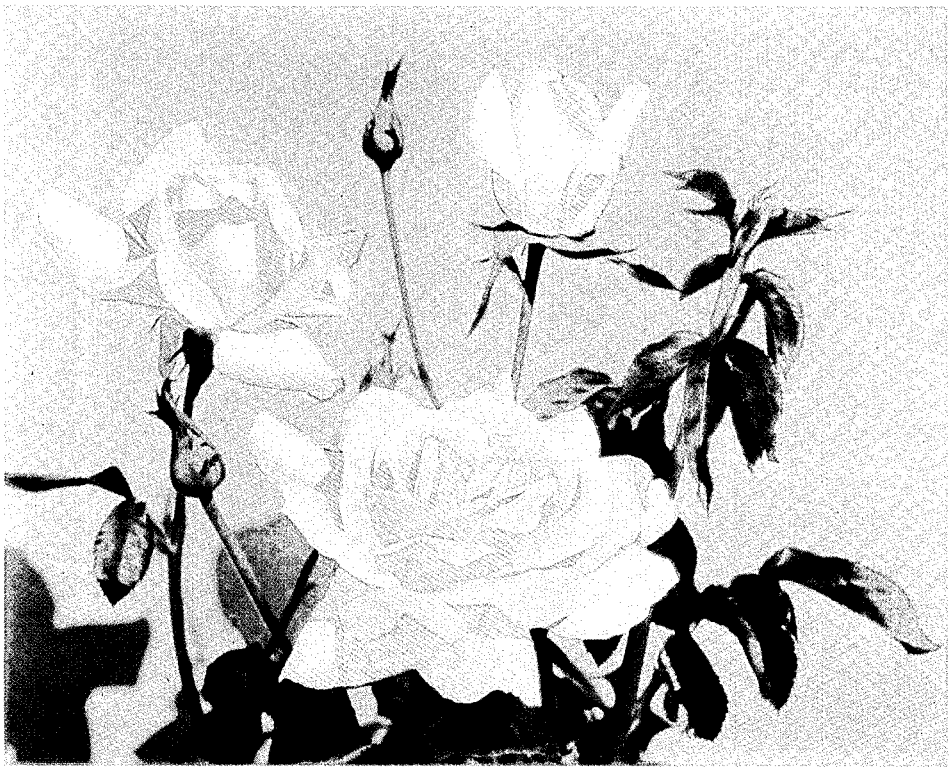
Inventor
W. E. Lammerts
By Robb & Robb
Attorneys Patented May 23, 1950 Plant Pat. 943

UNITED STATES PATENT OFFICE

943

ROSE PLANT

Walter E. Lammerts, La Canada, Calif., assignor, by mesne assignments, to Descanso Distributors, Inc., La Canada, Calif., a corporation of California Application March 15, 1949, Serial No. 81,418

1 Claim. (Cl. 47—61)

The present invention relates to a new and distinct variety of rose plant resulting from crossing two well-known and attractive varieties "Crimson Glory" (Pl. Pat. #105), a crimson bush rose, and "Captain Thomas" (Pl. Pat. #393), a lemon colored rose of the pillar type.

This new variety is characterized by its vigorous, upright, pillar type of growth, needing no supports, and reaching a height of eight to nine feet in one season, combined with the ability to flower as abundantly the first season after planting and thereafter as a hybrid tea rose. The following unique combination of characters makes this variety well adapted for outdoor cut flower production:

(1) The buds are medium long urn shaped.

(2) They are often borne singly or two to three on long (four to six foot) stems, even without disbudding. As many as fifteen or twenty flowers may be produced on the most vigorous stems.

(3) They open slowly to a large high centered fully double flower of scarlet to rose red color with petals well displayed and inner ones curved inward and thus covering the stamens.

(4) The flowers last six to seven days after cutting at ordinary room temperatures and fade attractively, thus remaining in good display condition.

(5) The bush and flowering stems are abundantly clothed with very large, leathery, glossy, mildew resistant, green foliage, and the flowering stems are almost completely free of thorns.

Though making a vigorous well clothed pillar type of rose if unpruned, this variety may be grown as a high bush by summer pruning as it sends up numerous canes from the base which flower abundantly on current season's growth.

This variety resembles "High Noon" (Pl. Pat. #704) somewhat in habit of growth as both varieties are vigorous, everblooming pillar roses. It differs from "High Noon" in having larger and more glossy foliage, which is much more resistant to mildew, a more upright sturdy cane growth, thus needing no support at all, fewer thorns, particularly on flowering stems, and a much more double flower of a scarlet to rose red to begonia rose color instead of a semi-double yellow flower.

Asexual reproduction shows that the foregoing characteristics hold true through succeeding propagations.

The following is a detailed description of this new variety, the color terminology being in accordance with Ridgway's Color Standards and Nomenclature, except where otherwise designated as taken from Maerz & Paul Color Chart:

Type: Hardy; tall; pillar; outdoor; seedling; for cut flowers and garden decoration.

Class: Hybrid tea.

Breeding: Seedling.

*Seed parent.*—"Crimson Glory" (Pl. Pat. #105).

*Pollen parent.*—"Captain Thomas" (Pl. Pat. #393).

Propagation: Holds its distinguishing characteristics through succeeding propagations by cuttings, grafting and budding.

*Flower*

Locality where asexually reproduced by budding and grown: La Canada, California.

Flowers borne: Often borne singly and two or three to stem; on strong, long stems, though as many as fifteen or twenty may occur on most vigorous stems.

Quantity of bloom: Abundant; outdoors.

Continuity: Continuous.

Fragrance: Moderate; centifolia.

Bud:

*Peduncle.*—Medium long; medium heavy; erect; medium reddish green; entirely smooth; numerous very small gray hairs.

*Before calyx breaks.*—*Size*—medium large. *Form*—short; pointed; ovid; without foliaceous appendages on the surface of the bud, but alternating sepals with two to three small lance-shaped appendages about one-eighth inch long; without foliaceous parts extending beyond the tip of the bud, but sepals simply lance pointed extending about one-fourth inch beyond tip of petals. *Color*—varying from Nopal Red (Plate I3*i*) to Carmine (Plate I1*i*), Ridgway.

*As calyx breaks.*—*Color*—Carmine (Plate I1*i*) to Pale Lemon Yellow (Plate IV23*b*) at base, Ridgway.

*As first petal opens.*—*Size*—medium. *Form*—long; urn-shaped. *Color*—outside: varying from Sweetbriar (Plate 1C4) to Begonia Gaiety (Plate 2K8), Maerz & Paul; inside: varying from Scarlet Red (Plate I3) to rose color (Plate XII71*b*), Ridgway.

*Openings.*—Opens up well; retarded by cold weather.

Bloom: Size, when fully open—large; 4 inches to 5 inches.

*Petalage.*—Double to very double; many petals, usually with no stamens showing; from 33 to 40 petals arranged regularly.

*Form.*—At first a high-centered flower, becoming more open to cupped, or remaining high centered; usually inner petals curve inward thus covering the stamens; outer petals rolled outward, and at maturity all except innermost petals rolled outward.

Petals: Thick, with inside and outside satiny.

*Shape.*—Outside—obovate with apex usually without notches though occasionally with two or three notches. Intermediate—obovate with apex usually without notches, though occasionally with two or three notches. Inside—ovate to lanceolate with apex.

*Color.*—Colors may be modified by being margined or penciled with white.

This description of a newly opened flower was made from a rose grown outdoors in the month of November at La Canada, California:

*Color.*—*Outside petal*—outside surface: Begonia Rose (Plate I1*b*) to Deep Rose Pink (Plate XII71*f*), Ridgway; inside surface: Dolly Pink (Plate 2K3), Maerz & Paul, to Rose Color (Plate XII71*b*) veined with Scarlet (Plate I1), Ridgway. *Intermediate petal*—outside surface: varying from an unnamed color shown in (Plate 1K7) which is two grades darker than Rose d'Althaea (Plate 1I7), Maerz & Paul, to Begonia Rose (Plate I1*b*), Ridgway; inside surface: Rose Red (Plate XII71) to Rose Color (Plate XII71*b*), Ridgway. *Inner petal*—outside surface: Rose Neyron (Plate 1J4), Maerz & Paul, to Begonia Rose (Plate I1*b*), Ridgway; inside surface: Rose Red (Plate XII71) to Rose Color (Plate XII71*b*), Ridgway. Each petal with narrow white margin. Some inner petals with Baryta Yellow (Plate IV21*f*), Ridgway, stripe in the center.

This description was made from a rose that was open for three days outdoors in the month of November at La Canada, California:

*Color.*—*Outside petal*—outside surface: varying from an unnamed color shown in (Plate 50F4) which is near Cosmos Pink (Plate 50D6) to Spring Beauty Pink (Plate 50J5), Maerz & Paul; inside surface: Spring Beauty Pink (Plate 50J5) to an unnamed color shown in (Plate 3F8) which is two grades lighter than Lotus Pink (Plate 3H8) at base of petal, Maerz & Paul. *Inside petal*—outside surface: Of an unnamed color shown in (Plate 1G3), Maerz & Paul, which is one grade more red and one grade lighter than France Rose Pink (Plate 1F4), Maerz & Paul; inside surface: Varying from Spring Beauty Pink (Plate 50J5) to Sea Pink (Plate 2I7) near base at petal, Maerz & Paul.

*General color effect.*—Newly opened flower—Scarlet Red (Plate I3) to Rose Red (Plate XII71) to Begonia Rose (Plate I1*b*), Ridgway. Three days open—Rose color (Plate XII71*b*), Ridgway.

*Behavior.*—Drop off cleanly; affected by hot weather. Cycle more rapid but color changes about the same except fading to lighter color.

*Flower longevity.*—On bush in garden—four days in November. Cut roses grown outdoors kept at living-room temperatures, six days in October.

*Reproductive organs*

Stamens: Medium number; arranged regularly about pistils.

Filaments: Medium length (¼ to ½ inches long); yellow to reddish; most with anthers. *Color*—Bittersweet Orange (Plate II9*b*) to Light Cadmium (Plate IV19), Ridgway.

Anthers: Small; yellow; open at various times. *Color*—Light Cadmium (Plate IV19) to Mustard Yellow (Plate XVI19*b*), Ridgway.

Pollen: Sparse; gold.

Pistils: Many.

Styles: Even; medium long; thin; bunched; columnar and all bent about at middle.

Stigma: Yellow.

Ovaries: All enclosed in calyx.

Hips: Flat with inconspicuous neck; yellow with russet; smooth; walls thin.

Sepals: Permanent; moderately long; spear-shaped; recurved. *Color*—inside varying from a Fern Green (Plate 21F5) to Asphodel Green (Plate 21J5), Maerz & Paul. Outside of an unnamed color shown in (Plate 21L9) which is 7 grades darker than the nearest named color Winter Green (Plate 21E9), Maerz & Paul.

Seeds: Few; medium size.

*Plant*

Foliage:

*Leaves.*—Compound of five to seven leaflets; very abundant; very large; very leathery and glossy.

*Leaflets.*—Oval with apex acute; mucronate; base round; margin simply serrate.

*Color.*—*Mature*—upper surface: normal; green; under surface: light; green. *Young*—upper surface: light; green bronze; under surface: light; green.

*Rachis.*—Medium heavy. Upper side grooved. Under side smooth.

*Stipules.*—Medium long; medium wide with short points turning out at an angle of more than 90°, recurved toward the stem.

*Disease.*—Resistant to mildew and blackspot.

Growth:

*Habit.*—Upright; much branched.

*Growth.*—Vigorous; 8 to 9 feet high in one season in La Canada, California.

*Canes.*—Heavy.

*Main stems.*—Green. *Thorns*—few; medium long; hooked slightly downward; with long, narrow base. *Prickles and hairs*—none.

*Branches.*—Gray green heavily tinged with purplish red. *Thorns*—very few; medium long; hooked downward; with long, narrow base; practically no thorns on upper part of flowering stems. *Prickles*—none. *Hairs*—many; small; gray.

*New shoots.*—Gray green heavily tinged with purplish red. *Thorns*—very few; medium long; hooked downward; with long, narrow base. *Prickles*—none. *Hairs*—many; very small; gray.

The distinctions between this new variety above disclosed and those of its parents are so obvious as to not require any great detail relative to such distinctions herein. It is sufficient to say that it is distinct from its parents by its pillar habit of growth, the color of the flowers, and number of petals. It is for this reason that the comparison with another pillar rose of this general type, namely, "High Noon" is made herein.

I claim:

A new and distinct variety of rose plant characterized as to novelty by its vigorous, upright, pillar type of growth; by its habit of flowering as abundantly the first season as does a hybrid tea rose; the urn shape buds; the production of as many as fifteen to twenty flowers on vigorous stems; the form and color of the high centered flowers; the lasting quality and attractive fading character of the cut flowers; its large, leathery, glossy and disease-resistant foliage; and the absence of thorns on the flowering stems, substantially as shown and described.

WALTER E. LAMMERTS.

No references cited.